(12) United States Patent
van Hal et al.

(10) Patent No.: US 9,932,825 B1
(45) Date of Patent: Apr. 3, 2018

(54) GAS CHROMATOGRAPH MASS SPECTROMETER FOR DOWNHOLE APPLICATIONS

(71) Applicant: SCHLUMBERGER TECHNOLOGY CORPORATION, Sugar Land, TX (US)

(72) Inventors: Ronald E. G. van Hal, Cambridge, MA (US); Albert Ballard Andrews, Wilton, CT (US); Jeffrey Crank, Cambridge, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/286,225

(22) Filed: Oct. 5, 2016

(51) Int. Cl.
| | |
|---|---|
| *E21B 49/00* | (2006.01) |
| *G01N 25/18* | (2006.01) |
| *E21B 49/08* | (2006.01) |
| *G01V 9/00* | (2006.01) |
| *G01N 30/72* | (2006.01) |

(52) U.S. Cl.
CPC ............... *E21B 49/08* (2013.01); *G01V 9/00* (2013.01); *E21B 2049/085* (2013.01); *G01N 25/18* (2013.01); *G01N 30/7206* (2013.01)

(58) Field of Classification Search
CPC .... E21B 49/005; E21B 49/085; E21B 49/088; E21B 47/00; B01D 19/0052; H01J 49/0027; H01J 49/004; H01J 49/26; G01N 30/72; G01N 30/7206; G01N 33/2823

USPC .......... 422/68.1, 80, 50; 702/6, 16; 250/281, 250/282; 73/152.04, 23.37; 96/101, 9
See application file for complete search history.

(56) References Cited

U.S. PATENT DOCUMENTS

| | | | | |
|---|---|---|---|---|
| 3,563,083 A | * | 2/1971 | Benz ................. | G01N 30/7206 73/23.37 |
| 4,739,654 A | | 4/1988 | Pilkington et al. | |
| 5,024,952 A | * | 6/1991 | Alsop ................ | B01D 17/0205 210/748.01 |
| 5,039,489 A | * | 8/1991 | Gleaves ................. | B01L 1/00 422/50 |
| 5,342,580 A | * | 8/1994 | Brenner .................. | G01N 7/04 422/88 |
| 5,401,962 A | | 3/1995 | Ferran | |
| 5,596,193 A | | 1/1997 | Chutjian et al. | |
| 5,719,393 A | | 2/1998 | Chutjian et al. | |
| 6,469,298 B1 | | 10/2002 | Ramsey et al. | |

(Continued)

*Primary Examiner* — David A Vanore

(57) ABSTRACT

Wellbore tools in accordance with the present disclosure may include a gas chromatograph; and a mass spectrometer, wherein the mass spectrometer is configured to operate at a pressure greater than $10^{-2}$ Torr. Systems in accordance with the present disclosure may include a gas chromatograph; and a mass spectrometer, wherein the mass spectrometer is configured to operate at a pressure greater than $10^{-2}$ Torr. Methods in accordance with the present disclosure may include emplacing a wellbore tool in a wellbore, the wellbore tool containing a gas chromatograph and a mass spectrometer, wherein the mass spectrometer is configured to operate at a pressure greater than $10^{-2}$ Torr; drawing a sample of a fluid from the wellbore into the wellbore tool; and determining a molecular weight of one or more components of the fluid.

19 Claims, 18 Drawing Sheets

(56) References Cited

U.S. PATENT DOCUMENTS

| | | | |
|---|---|---|---|
| 6,576,197 B1* | 6/2003 | Windhab | B01J 8/001 |
| | | | 422/68.1 |
| 6,670,605 B1 | 12/2003 | Storm, Jr. et al. | |
| 6,675,101 B1* | 1/2004 | Shray | E21B 47/00 |
| | | | 702/6 |
| 6,751,555 B2* | 6/2004 | Poedjono | G01V 1/44 |
| | | | 702/16 |
| 6,762,406 B2 | 7/2004 | Cooks et al. | |
| 6,933,498 B1 | 8/2005 | Whitten et al. | |
| 7,219,541 B2 | 5/2007 | DiFoggio | |
| 7,384,453 B2 | 6/2008 | Bostrom et al. | |
| 7,458,257 B2 | 12/2008 | Pop et al. | |
| 7,600,413 B2 | 10/2009 | Shah et al. | |
| 7,654,130 B2 | 2/2010 | Shah et al. | |
| 7,658,092 B2 | 2/2010 | Bostrom et al. | |
| 7,752,906 B2 | 7/2010 | Pop et al. | |
| 7,772,546 B2 | 8/2010 | Jackson | |
| 8,056,408 B2 | 11/2011 | Pop et al. | |
| 8,145,429 B2 | 3/2012 | DiFoggio et al. | |
| 8,250,904 B2 | 8/2012 | Shah et al. | |
| 8,512,457 B2 | 8/2013 | Steinecker et al. | |
| 8,525,111 B1 | 9/2013 | Brown et al. | |
| 8,536,524 B2* | 9/2013 | Pomerantz | H01J 49/26 |
| | | | 250/281 |
| 8,805,614 B2 | 8/2014 | Andrews et al. | |
| 8,816,272 B1 | 8/2014 | Brown et al. | |
| 8,878,127 B2 | 11/2014 | Ramsey et al. | |
| 8,912,000 B2 | 12/2014 | Daniel et al. | |
| 8,921,774 B1 | 12/2014 | Brown et al. | |
| 8,939,021 B2* | 1/2015 | Daniel | E21B 49/10 |
| | | | 73/152.04 |
| 8,955,375 B2 | 2/2015 | DiFoggio et al. | |
| 8,968,560 B2 | 3/2015 | Steinecker | |
| 9,093,253 B2 | 7/2015 | Bartfay-Szabo et al. | |
| 9,099,286 B2 | 8/2015 | Brown et al. | |
| 9,528,366 B2* | 12/2016 | Selman | E21B 47/022 |
| 9,528,367 B2* | 12/2016 | Selman | E21B 47/06 |
| 9,528,372 B2* | 12/2016 | Selman | E21B 49/088 |
| 2010/0181471 A1 | 7/2010 | Pop et al. | |
| 2014/0260586 A1* | 9/2014 | Van Hal | E21B 49/082 |
| | | | 73/152.07 |
| 2014/0263999 A1 | 9/2014 | Ramsey | |
| 2015/0200083 A1 | 7/2015 | Brown et al. | |
| 2017/0138136 A1* | 5/2017 | Ochoa | B01D 19/0042 |

* cited by examiner

FIG. 6.1
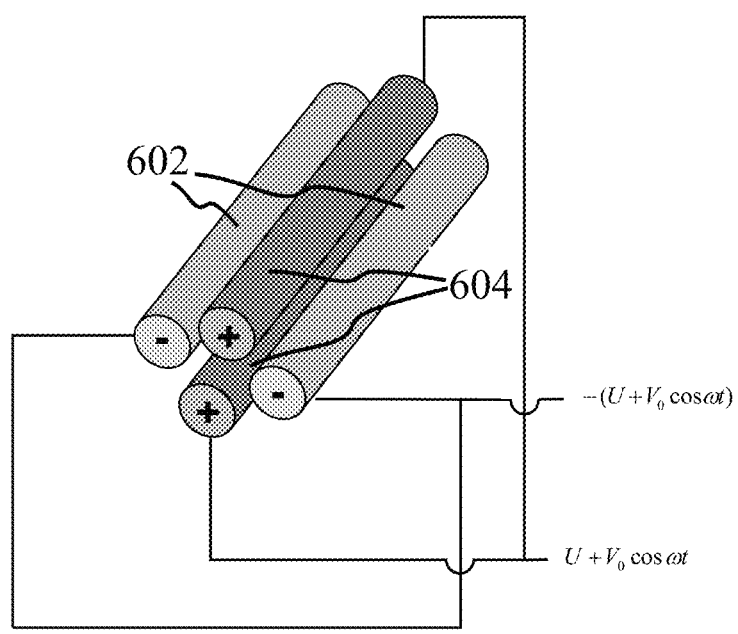
FIG. 6.2
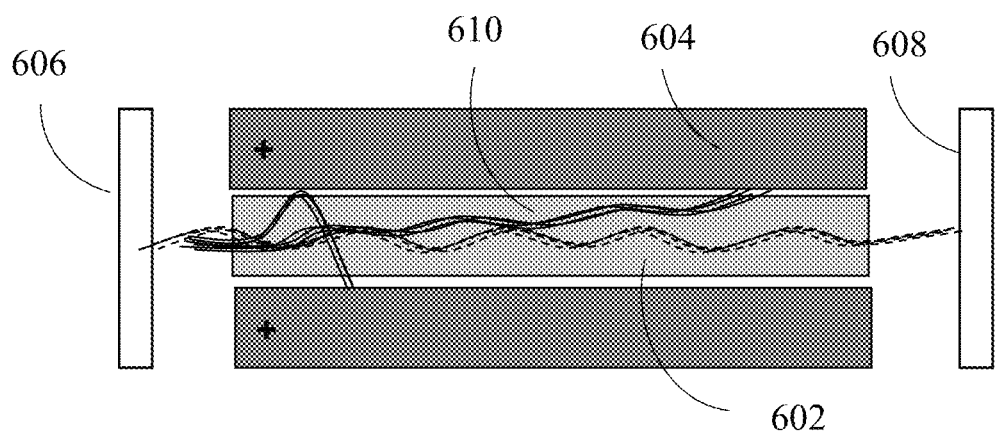

GAS CHROMATOGRAPH MASS SPECTROMETER FOR DOWNHOLE APPLICATIONS

BACKGROUND

As a wellbore is being prepared, samples of formation fluids may be obtained from downhole and analyzed onsite or sent to a full-scale laboratory. Analysis of the formation fluids may be beneficial for a variety of reasons including quantifying the quality and amount of the fluids and gasses entering the wellbore, assessing wellbore conditions for equipment installation downhole, and ensuring safe well site operation. The use of downhole measurement tools may be employed as operators seek to eliminate the need to obtain and transport samples of the formation fluids to the laboratory for further detailed analysis.

The analysis of wellbore fluids and gasses onsite may provide information about the maturity and nature of hydrocarbons in the accumulated source, compartmentalization of intervals in the reservoir being drilled, and oil quality, as well as information regarding production zones, lithology changes, history of reservoir accumulation, or seal effectiveness. However, downhole analysis using wellbore tools may be complicated by a number of factors. Wellbores may be small diameter holes having a diameter of approximately five inches or less when cased, which may constrain the geometry of the wellbore tool components. In addition, operating conditions for wellbore tools may be stringent, requiring designs that endure vibrations, elevated temperatures and high pressure environments.

SUMMARY

This summary is provided to introduce a selection of concepts that are described further below in the detailed description. This summary is not intended to identify key or essential features of the claimed subject matter, nor is it intended to be used as an aid in limiting the scope of the claimed subject matter.

In one aspect, wellbore tools in accordance with the present disclosure may include a gas chromatograph having a column configured to separate a fluid sample into at least partially separated components, a rotary valve configured to inject the fluid sample into the gas chromatograph, and a mass spectrometer configured to receive the at least partially separated components from the gas chromatograph. The mass spectrometer is configured to operate downhole at a pressure greater than $10^{-2}$ Torr and includes at least one of (a) an ion trap analyzer and (b) a quadrupole mass analyzer.

In another aspect, systems in accordance with the present disclosure may include a gas chromatograph having a column configured to separate a fluid sample into at least partially separated components, a rotary valve configured to inject the fluid sample into the gas chromatograph, and a mass spectrometer configured to receive the at least partially separated components from the gas chromatograph. The mass spectrometer is configured to operate at a pressure greater than $10^{-2}$ Torr and includes at least one of (a) an ion trap analyzer and (b) a quadrupole mass analyzer.

In another aspect, methods in accordance with the present disclosure may include emplacing a wellbore tool in a wellbore. The wellbore tool includes a gas chromatograph having a column configured to separate a fluid sample into at least partially separated components, a rotary valve configured to inject the fluid sample into the gas chromatograph, and a mass spectrometer configured to receive the at least partially separated components from the gas chromatograph. The mass spectrometer is configured to operate downhole at a pressure greater than $10^{-2}$ Torr and includes at least one of (a) an ion trap analyzer and (b) a quadrupole mass analyzer. The method further includes drawing the fluid sample from the wellbore into the wellbore tool and operating the gas chromatograph and the mass spectrometer to determine a molecular weight of one or more of the at least partially separated components of the fluid sample.

Other aspects and features of the disclosure will be apparent from the following description and the appended claims.

BRIEF DESCRIPTION OF FIGURES

FIGS. 6.1 and 6.2 are schematic representations of a quadrupole mass analyzer in accordance with the present disclosure.

DETAILED DESCRIPTION

Figure 1:
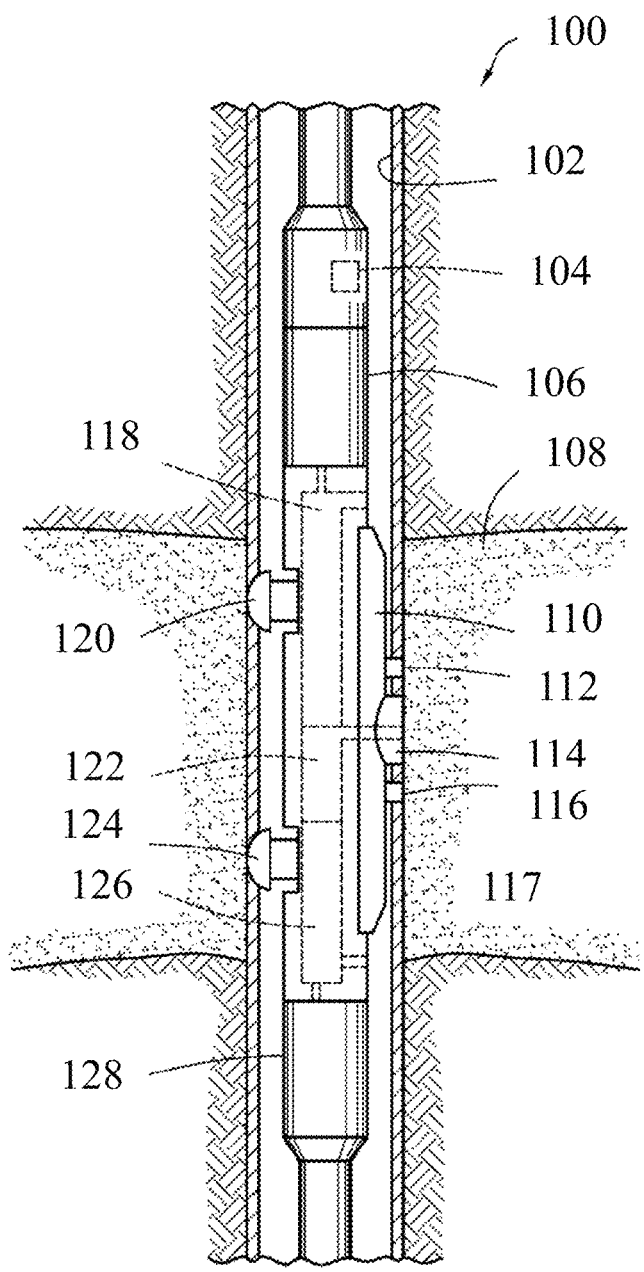
FIG. 1 is a schematic depicting a wellbore tool in accordance with embodiments of the present disclosure.

This disclosure relates generally to methods and tools for analyzing formation fluid and gas compositions. More particularly, this disclosure relates to the determination of a formation fluid composition using a gas chromatograph and a mass spectrometer. Mass spectrometers in accordance with the present disclosure may be configured to operate at relatively high pressures, such as above $10^{-3}$ Torr. In one or more embodiments, instrument components in accordance with the present disclosure may have small overall footprints that allow the components to be installed in downhole tools.

Devices in accordance with the present disclosure may be configured for combined gas chromatography and mass spectroscopy optimized for relatively high pressure operation. Gas chromatographs use chromatographic columns to separate molecular species within a sample fluid and thereby to extract information about the sample fluid. A chromatographic column has a stationary phase fixed inside the column and a mobile phase which is a carrier gas, such as, helium that flows through the column. The sample is collected, injected into the column and then transported by the carrier gas into and through the column. If the sample is in a liquid state, the sample may first be injected into a vaporization chamber to be vaporized then transported through the column. As a sample progresses through the column, the individual molecular components are slowed down based on their affinity to the stationary phase. At the outlet of the column, a detector measures the quantity of each component as it exits the column. The calibrated retention time, i.e., the time a component spends in the column, identifies the component.

In one or more embodiments, devices may include a gas chromatograph may be used in combination with a detector such as a thermal conductivity detector (TCD). Standard GC-TCD configurations may have a detection limit of about 500 ppm, which may be limited in resolution and lack the ability to identify individual components of fluids and gases detected downhole. In some embodiments, a mass spectrometer may be used in combination with GC-TCD to identify additional fluid and gas components, and may increase measurement sensitivity and lower detection limits of the device. Lower detection limits for hydrogen sulfide, mercaptans, corrosion-inducing agents, and oxidants may increase worksite safety and enable an operator to make informed decisions about selection of wellbore casing and other tools depending on expected levels of oxidative materials present within a given wellbore.

Devices in accordance with the present disclosure may be configured as part of a downhole tool. While standard mass spectrometers use turbo-molecular pumps to generate molecular flow conditions such as below $10^{-4}$ Torr, the pumps used to achieve these pressures are vulnerable to shock and vibration, and malfunctions of rotors and or bearings under high pressure, high temperature conditions, and corrosion in the presence of oxidants and other incompatible chemicals that may be present in wellbore fluids. However, devices in accordance with the present disclosure may be configured to be more robust against shock and vibration and to withstand higher operating temperatures than encountered in surface measurements, such as those present in a downhole environment. For example, operation at higher pressures in a viscous or laminar flow regime above $>10^{-3}$ Torr may enable mass spectrometers in accordance with the present disclosure to perform using scroll pumps and other components design to operate under harsh conditions.

In one or more embodiments, wellbore tools in accordance with the present disclosure may include a testing-while-drilling. With particular respect to FIG. 1, a testing-while-drilling device 100 may be provided into a wellbore, which may include a stabilizer with one or more blades 110 configured to engage a wall of the wellbore 110. The testing-while-drilling device 100 may be provided with a plurality of backup pistons 124 configured to assist in applying a force to push and/or move the testing-while-drilling device 100 against the wall of the wellbore 102. A probe assembly 114 may extend from the stabilizer blade 110 of the testing-while-drilling device 100. The probe assembly 114 may be configured to selectively seal off or isolate selected portions of the wall of the wellbore 102 to fluidly couple to an adjacent formation 117. Thus, the probe assembly 114 may be configured to fluidly couple components of the testing-while-drilling device 100, such as pumps 126 and/or 118, to the adjacent formation 117. Once the probe assembly 114 fluidly couples to the adjacent formation 117, various measurements may be conducted. For example, a pressure parameter may be measured by performing a pretest. Alternatively, or additionally, a sample may be withdrawn from the formation 117 via the probe assembly 114, and this sample may be analyzed using the ionization and spectrometry methods described above, possibly in conjunction with an ionization and/or spectrometry device also positioned within the device 100 and/or another component of the drill string.

The pump 118 may be used to draw subterranean formation fluid 108 from the formation 117 into the testing-while-drilling device 110 by the probe assembly 114. The fluid may thereafter be expelled through a port into the wellbore, or it may be sent to one or more fluid analyzers disposed in a sample analysis module 492, which may receive the formation fluid for subsequent analysis. Fluid analyzers may include one or more spectrometers and analyzers to interpret spectral data therefrom, such as to determine fluid composition utilizing the ionization and spectrometry methods in accordance with the present disclosure. The sample analysis module 106 may also be configured in some embodiments to perform such analysis on fluid obtained from the wellbore and/or drill string. For example, the sample analysis module 106 may be configured for use in mud-gas logging operations, wherein gas extracted from mud before and/or after the bit is analyzed to determine composition and/or concentrations; as described herein.

The stabilizer blade 110 of the testing-while-drilling device 100 may be provided with a plurality of sensors 112, 116 disposed adjacent to a port of the probe assembly 114. The sensors 112, 116 may be configured to determine petrophysical parameters such as saturation levels of a portion of the formation 117 proximate the probe assembly 114. For example, the sensors 112 and 116 may be configured to measure electric resistivity, dielectric constant, magnetic resonance relaxation time, nuclear radiation, and/or combinations thereof.

The testing-while-drilling device 100 may include a fluid sensing unit 122 through which the obtained fluid samples and/or injected fluids may flow, and which may be configured to measure properties of the flowing fluid. It should be appreciated that the fluid sensing unit 122 may include any combination of conventional and/or future-developed sensors within the scope of the present disclosure.

A downhole control system 104 may be configured to control the operations of the testing-while-drilling device 100. For example, the downhole control system 104 may be configured to control the extraction of fluid samples from the formation 117, wellbore and/or drill string, the analysis thereof, and any pumping thereof, for example, via the pumping rate of the pumps 126 and/or 118.

The downhole control system 104 may be configured to analyze and/or process data obtained from the downhole sensors and/or disposed in the fluid sensing unit 122 or from the sensors 112, and/or the fluid analysis module 106. The downhole control system 104 may be further configured to store measurement and/or processed data, and/or communicate measurement and/or processed data to another component and/or the surface for subsequent analysis.

While the testing-while drilling device 100 is depicted with one probe assembly, multiple probes may be provided with the testing-while drilling device 100 in accordance with the present disclosure. For example, probes of different inlet sizes, shapes (e.g., elongated inlets) or counts, seal shapes or counts, may be provided. Wellbore tools in accordance with the present disclosure may be designed to include the detection components on a logging sonde or drill string.

Figure 2:
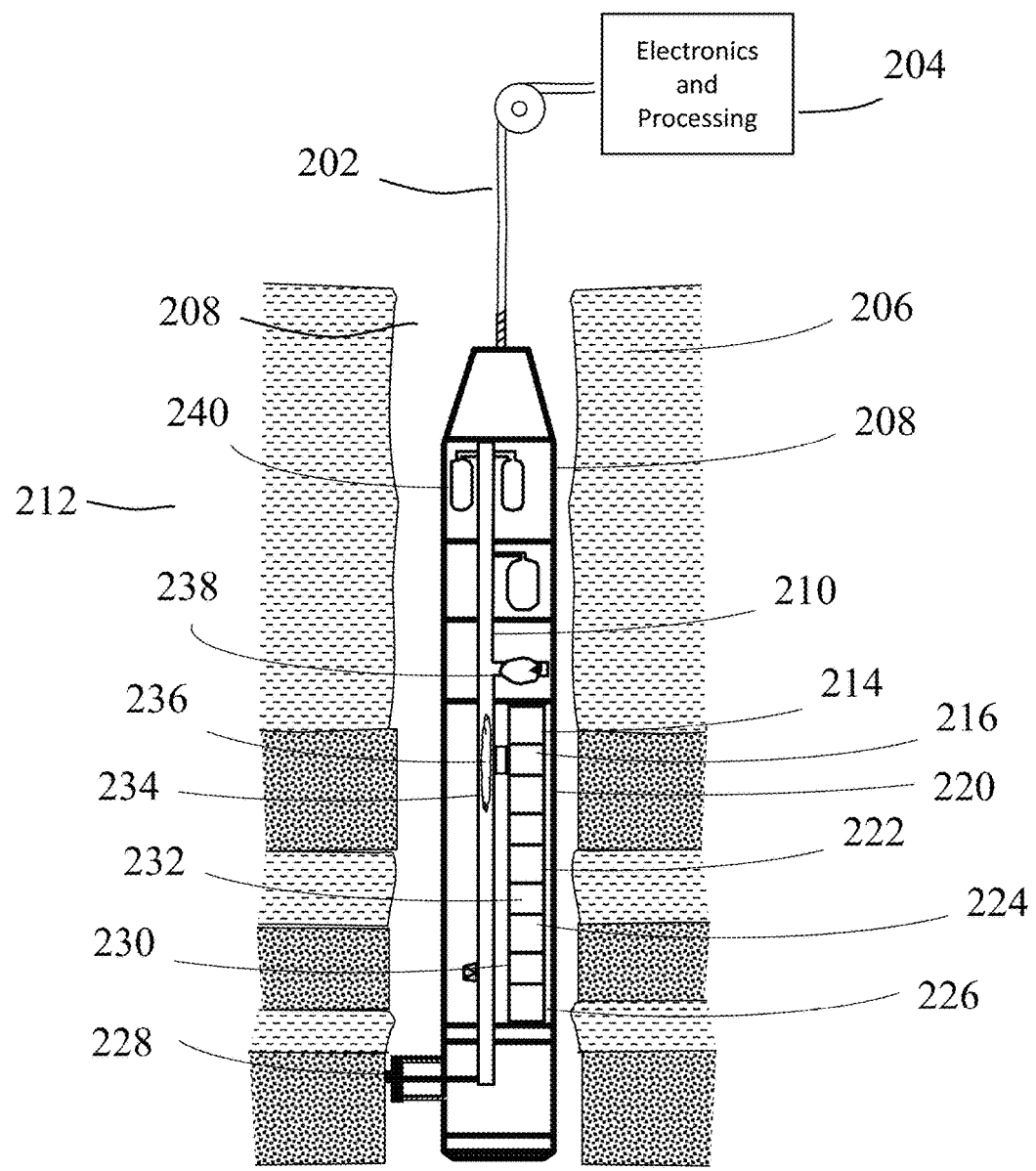
FIG. 2 is a schematic depicting a wireline tool in accordance with embodiments of the present disclosure.

Turning to FIG. 2, an example well site system according to one or more aspects of the present disclosure is shown. The well site may be situated onshore (as shown) or offshore. A wireline tool 212 may be configured to measure a portion of a wall of a wellbore penetrating a subsurface formation 206. A wireline tool 212 may be suspended in the wellbore 208 from a lower end of a multi-conductor cable 202 that may be spooled on a winch at the surface. Cable 202 may be communicatively coupled to an electronics and processing system 204. The electronics and processing system 204 may include a controller having an interface configured to receive commands from a surface operator. In some cases, the electronics and processing system 204 may further include a processor configured to implement one or more aspects of the methods described herein.

The example wireline tool 212 may include a tool housing 208 protecting the internals, a central flow line 210 running through the body of the tool connecting the sample bottle 240 to other components such as fluid pump 238 and probe assembly 228. During operation, a sample 234 may be drawn into sample inlet and/or injection valve 236 and carried to the analytical module. The analytical module contains a gas source 214 in connection with a vaporization chamber 216 and chromatography column 220 in line with a thermal conductivity detector (TCD) 222. The mass spectrometer module contains the mass analyzer 224, which is pressure-regulated by vacuum pump 226.

Figure 3:
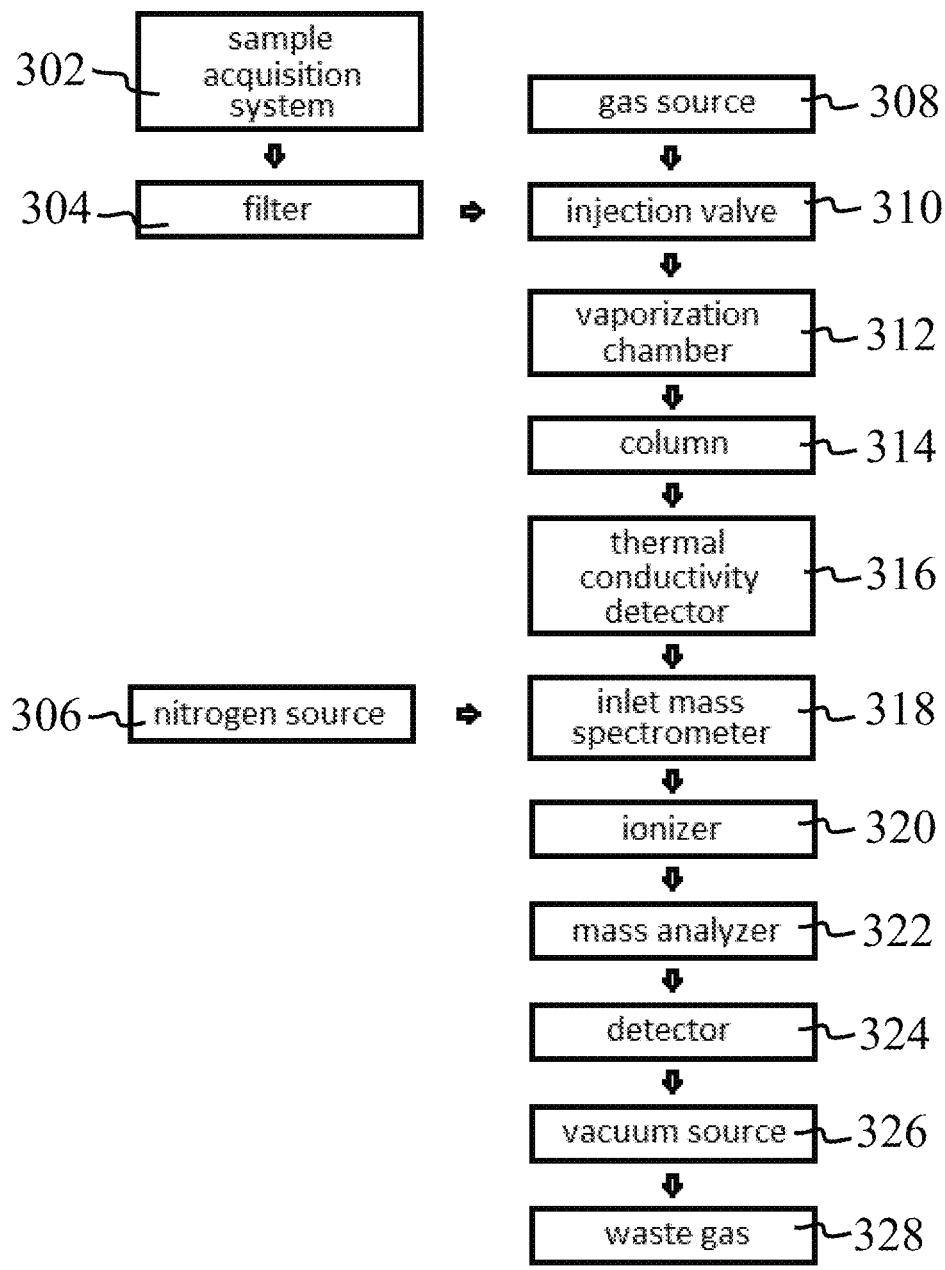
FIGS. 3 and 4 are flow diagrams indicating various tool configurations in accordance with embodiments of the present disclosure.

Tools in accordance with the present disclosure may be arranged in various configurations between the gas chromatograph, detector, and mass spectrometer. With particular respect to FIG. 3, a flow diagram is shown indicating a possible configuration of a wellbore analysis tool in accordance with the present disclosure. To begin a downhole measurement, a sample is drawn from the wellbore using a sample acquisition system at 302 and, in some embodiments, passed through a filter 304 to remove solid debris and other materials. A gas emitted from a gas source 308 is then used to carry a sample introduced by the injection valve 310 into the vaporization chamber 312. The vaporized sample and carrier gas are then passed through the chromatography column 314 to separate the sample into various components.

Depending on the system configuration, the outlet of the gas chromatography column may send the sample to a thermal conductivity detector 316 for component analysis. The outlet of the thermal conductivity detector may be connected to the inlet of a mass spectrometer 318 in some embodiments, which may receive the sample components, along with gas from a source 306. In one or more embodiments, an ionizable gas such as nitrogen may be added from source 306 to increase sample ionization prior to introduction into the mass spectrometer module of the wellbore tools.

However, gas supplementation from 306 may be omitted in some embodiments in which sample volume and carrier gas permit MS measurement. In some embodiments, the thermal conductivity detector may be omitted and the sample may exit the chromatography column 314 and pass directly to the inlet of the mass spectrometer 318. Once the sample passes into the mass spectrometer from inlet 318, vacuum generated from a vacuum source 326 draws the sample through ionizer 320, into the mass analyzer 322, and to MS detector 324. Following measurement, the sample leaves the system and is discarded as waste gas 328. In one or more embodiments, one or both of detectors 316 and 324 may be monitored and/or controlled by a computer processor.

Figure 4:
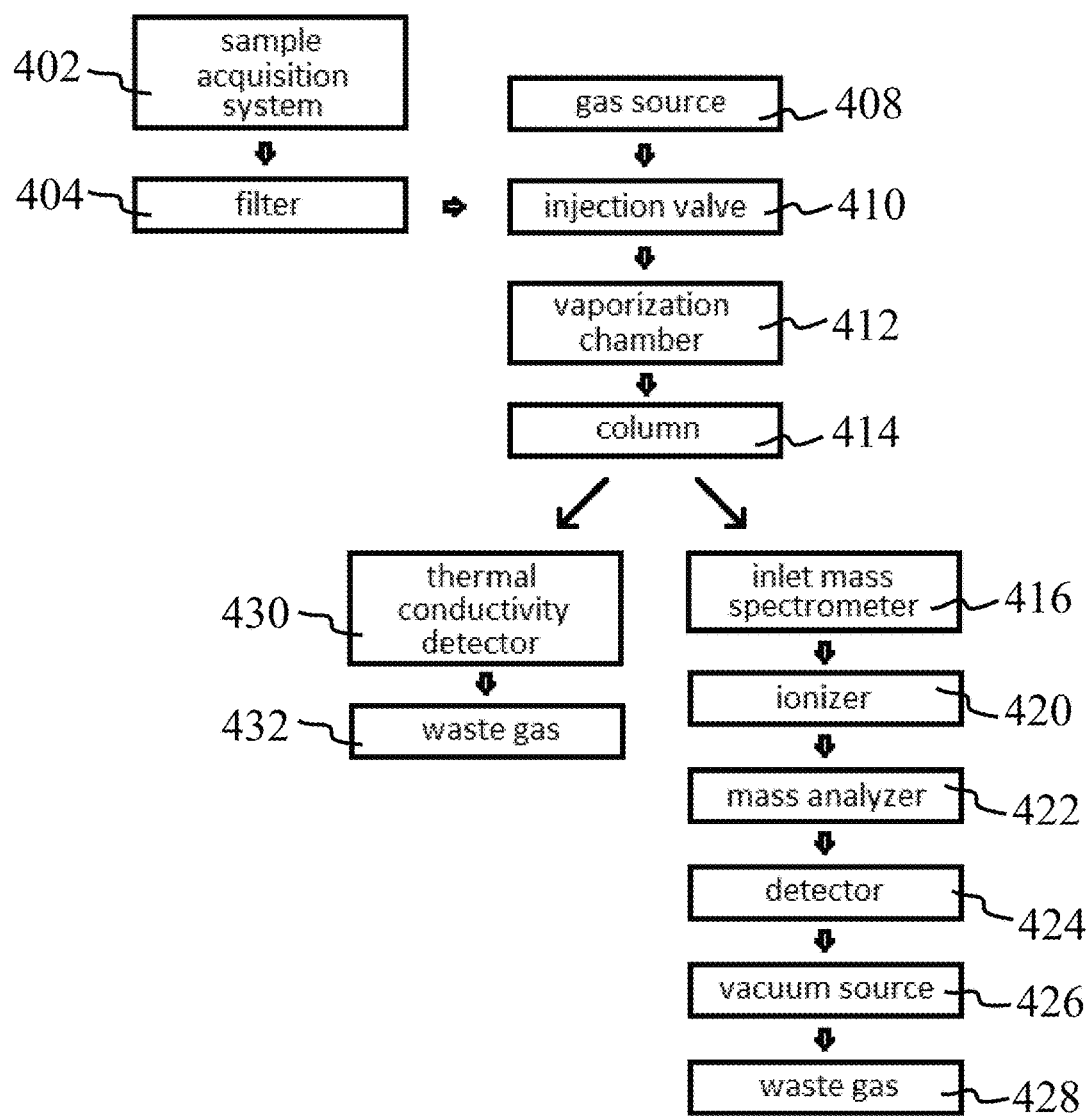

With particular respect to FIG. 4, a flow diagram is shown indicating another configuration of a wellbore analysis tool in accordance with the present disclosure. To begin a downhole measurement, a sample is drawn from the wellbore using a sample acquisition system at 402 and, in some embodiments, passed through a filter 404 to remove solid debris and other materials. A gas emitted from a gas source 408 is then used to carry a sample introduced by the injection valve 410 into the vaporization chamber 412. The vaporized sample and carrier gas are then passed through the chromatography column 414 to separate the sample into various components.

As the sample exits the chromatography column 414, the sample may be divided into two streams. A first stream may be directed to a thermal conductivity detector 430 and discarded as waste gas 432. The second stream may direct the sample to the inlet of a mass spectrometer 416. Once the sample passes into the mass spectrometer from inlet 416, vacuum generated from a vacuum source 426 may draw the sample through ionizer 420, into the mass analyzer 422, and to MS detector 424. Following measurement, the sample leaves the system and is discarded as waste gas 428. In one or more embodiments, one or both of detectors 430 and 424 may be monitored and/or controlled by a computer processor.

Figure 5:
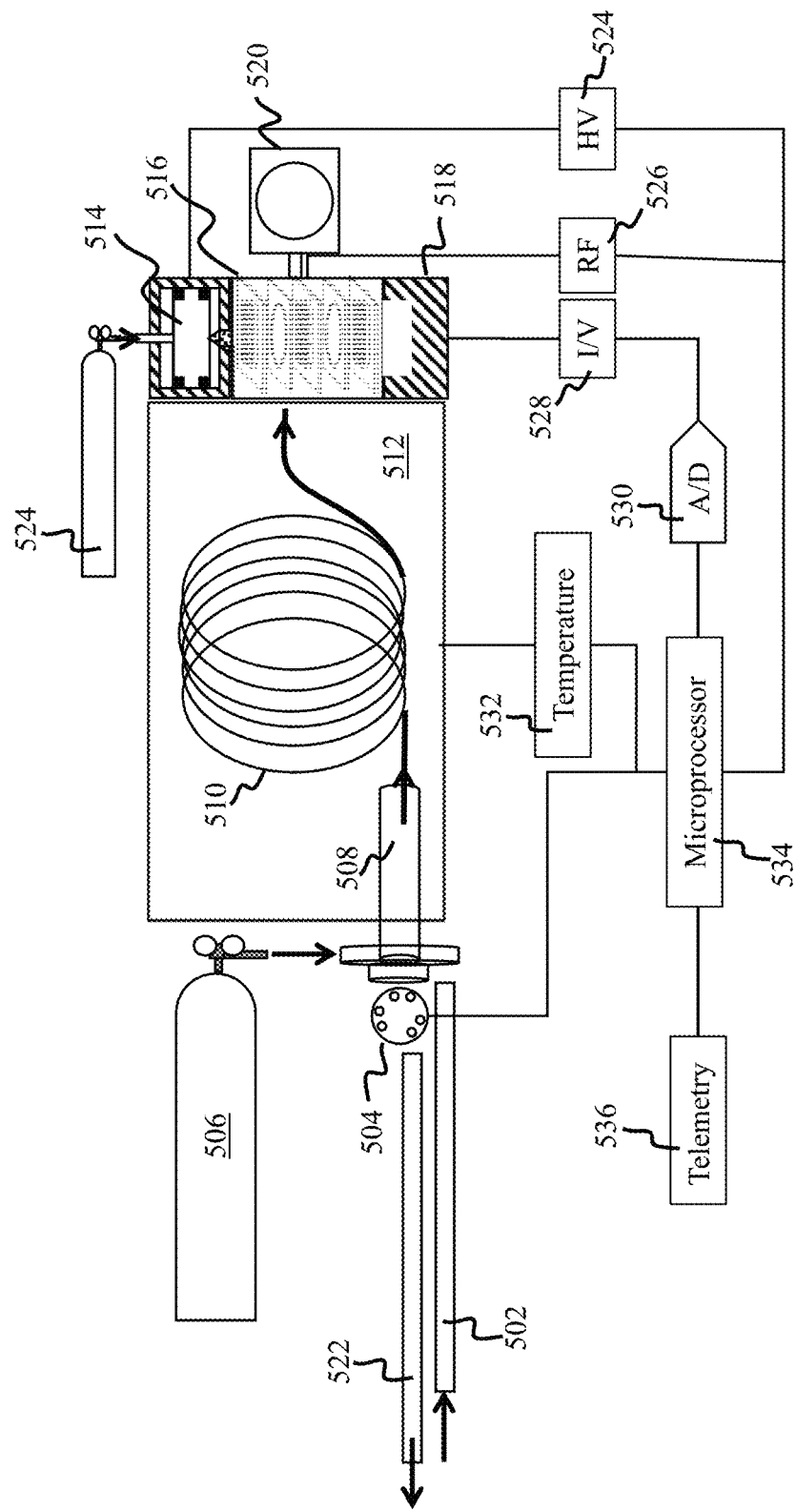
FIG. 5 is a schematic representations of combined gas chromatograph and mass spectrometers in accordance with embodiments of the present disclosure.

With particular respect to FIG. 5, an embodiment of a GC-MS in accordance with the present disclosure is shown. During operation, a flow line 502 initially contains the sample prior to passage into the GC by injection valve 504. The injection valve 504, as well as the other injection valves discussed herein, are rotary valves, although in some examples other types of valves may be provided. The sample is passaged with a carrier gas emitted by gas source 506 into vaporization chamber 508 and the vaporized sample is separated into various components in column 510, which may be heated to maintain vaporization using oven 512. Following passage through the GC module, the vaporized sample components are carried into the mass spectrometer component containing a mass analyzer 516 such as a cylindrical ion trap (CIT). Once the sample is in the mass spectrometer module, the sample is ionized by an ionization source 514 such as a glow discharge ionizer (GDI), further separated by the mass analyzer 516, and passaged to a detector 518 such as a Faraday cup. In some embodiments, the sample exiting the GC module may be combined with an ionizable gas from secondary gas source 524. The mass spectrometer may also maintain vacuum during operation using a vacuum pump 520 such as a scroll pump or other vacuum source. Following analysis, the sample components may pass into waste line 522 for appropriate disposal or recycling.

FIG. 5 also shows a schematic diagram of various electronic components adapted for use in connection with the exemplary fluid analysis sampling in accordance with embodiments of the present disclosure. According to at least one embodiment, a microprocessor 534 generally represents any form of computing or controlling device capable of performing any number of logic and/or controlling operations. In many embodiments, microprocessor 534 addresses and controls the operation of the valve 504, carrier gas source 506, temperature controller 532, radio frequency generator 526 and high voltage (HV) source 524. In some embodiments, microprocessor 534 may also be configured to receive telemetry data for a wellbore under analysis.

Although not specifically illustrated in FIG. 5, the output of reference detector 518 may be connected to one or more current amplifiers (I/V) 528, and/or an analog-to-digital (A/D) converter 530. A current amplifier 528 may convert the signal detected by detector 518 into a voltage, and/or an A/D converter 530 may convert the analog signal into a digital one. The resulting signal, which in many embodiments digitally represents the intensity of ion current detected by detector 518, may then be supplied to microprocessor 534 for use in computing the peak areas of the MS, FID or TCD spectrum of the vaporized fluid (gas) sample. Thus, in accordance with the signals supplied by the MS, TCD or FID, microprocessor 534 computes the presence and/or amount of any of a number of chemical compositions in vaporized fluid or gas sample.

Although the foregoing descriptions of FIG. 5 have been provided with reference to discrete elements and circuits, one of skill in the art having the benefit of this disclosure will recognize that one or more of these discrete circuits may be combined into a single integrated circuit or chip. For example, while transimpedance amplifier 528 and A/D converter 530 have been illustrated as discrete elements, the function of these two circuits may be combined into a single integrated circuit, resulting in increased savings in space and efficiency. The temperature and operation of the column 510 in oven 512 may be controlled by temperature controller 532, which may in turn be controlled by microprocessor 534.

With respect to FIG. 6.1, a first view of a quadrupole mass analyzer in accordance with embodiments of the present disclosure is shown. The interior of the mass analyzer contains an arrangement of four cylindrical electrodes with two electrodes 602 connected to negative polarity DC−RF voltage supply, and the remaining electrodes 604 connected to positive polarity DC+RF voltage. With particular respect to FIG. 6.2, a cross-section of the quadruple mass analyzer is shown during operation. A sample entering the mass analyzer is converted to ions by ionization source 606 and passaged into the channel created by positive electrodes 604 and negative electrodes 602, where the trajectory of the ions are modified, depending on molecular weight or conformation, for example, in a RF voltage-dependent fashion. Following separation by the arranged electrodes, the separated ions pass to detector 608. Representative ion trajectories are shown at 610.

Figure 7:
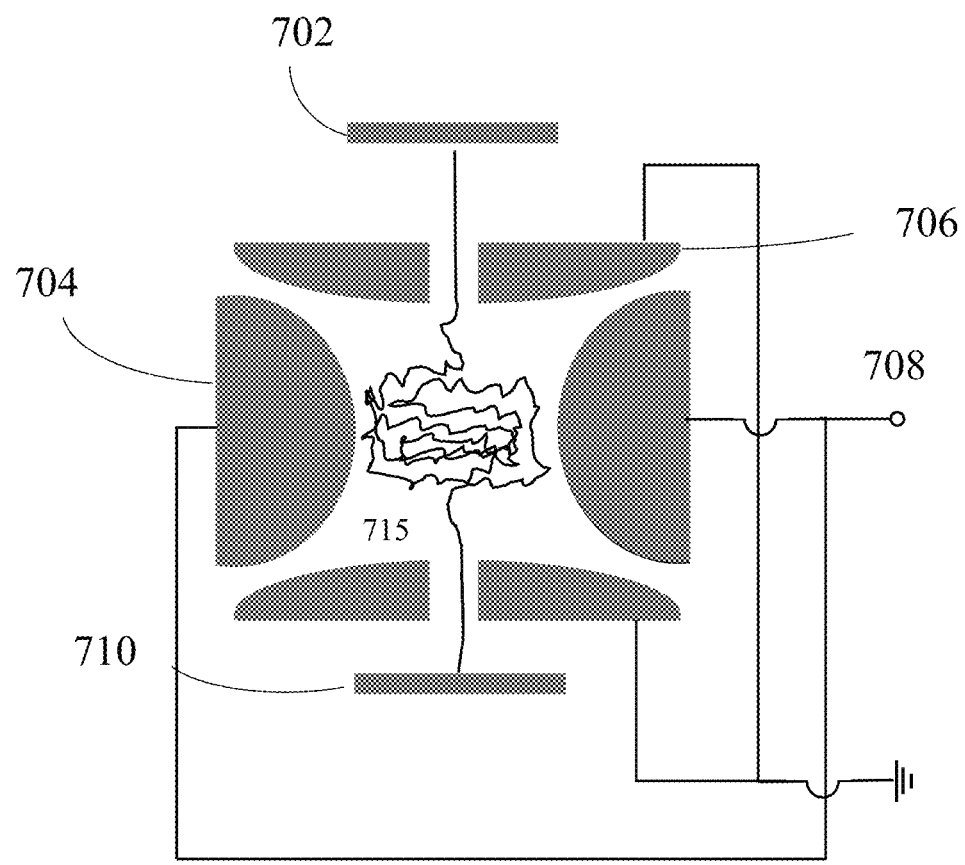
FIG. 7 is a schematic representation of a ion trap mass analyzer in accordance with embodiments of the present disclosure.

With respect to FIG. 7, a quadrupole ion trap mass analyzer is shown. A sample entering the mass analyzer encounters an ionization source 702 and the resulting ions are passed into the field of ring electrode 704 having end caps 706. Once charged ions enter the mass analyzers, ions are circulated in the space within the center of the electrode, and the RF voltage supply 708 is modulated to selectively emit ions that are passed to detector 710 in a controlled fashion. A representative ion trajectory is shown at 715.

Figure 8:
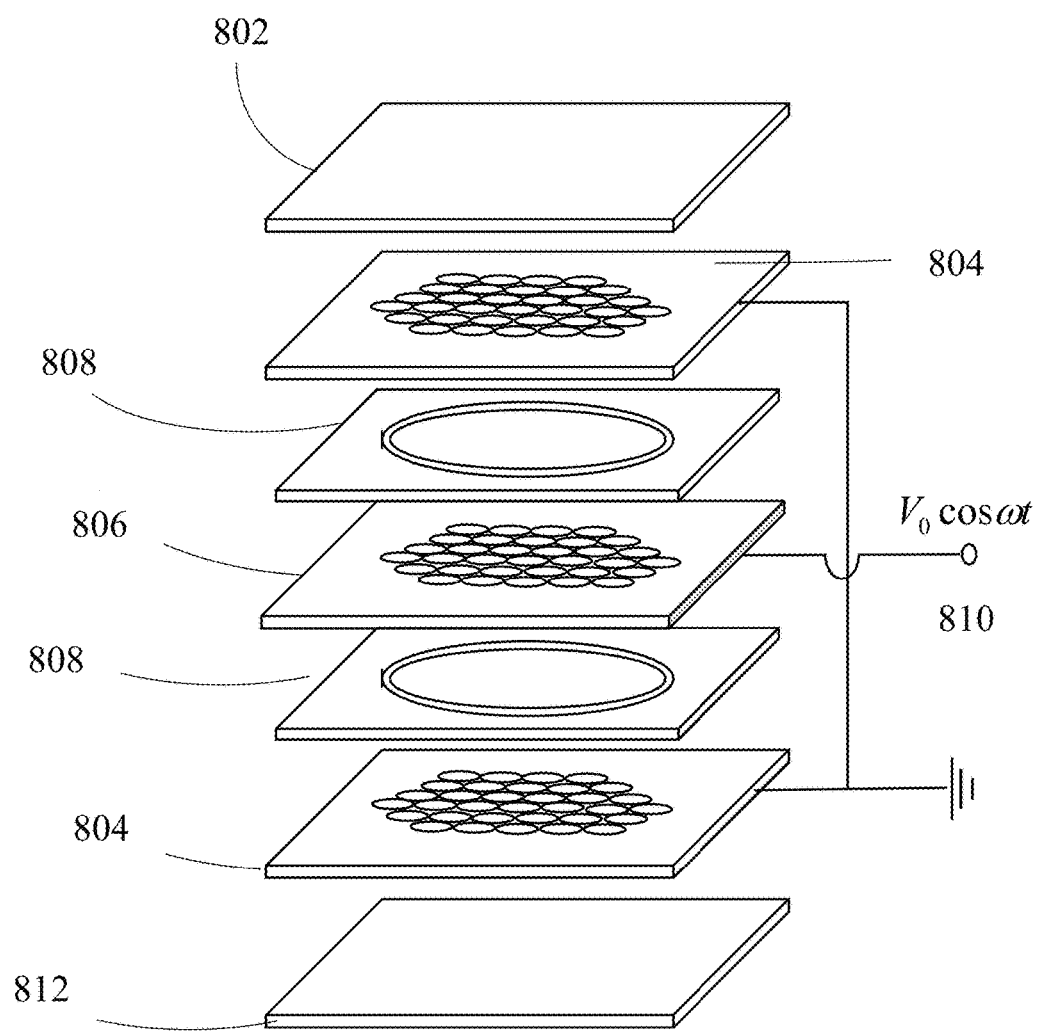
FIG. 8 is a schematic representation of a cylindrical ion trap mass analyzer in accordance with embodiments of the present disclosure.

With respect to FIG. 8, an exploded view of a cylindrical ion trap (CIT) mass analyzer is shown in accordance with embodiments of the present disclosure. A sample entering the CIT passes the ionization source 802, end cap 804, and through a plurality of ring electrodes 806 and insulators 808 before reaching the detector 812. The CIT mass analyzer is controlled by an RF voltage supply 810 that may be modulated to resolve molecular species of varying weights and conformations.

In one or more embodiments mass spectrometers may operate under temperature ramp or constant temp operational modes. In some embodiments, variables such as vacuum strength or RF may be adjusted to optimize the outcome of each measurement. Furthermore, to expand the detection range, the sample concentration can be reduced by dilution or other methods. Adaptations can be done automatically as a gradual or a stepwise change.

Figure 9:
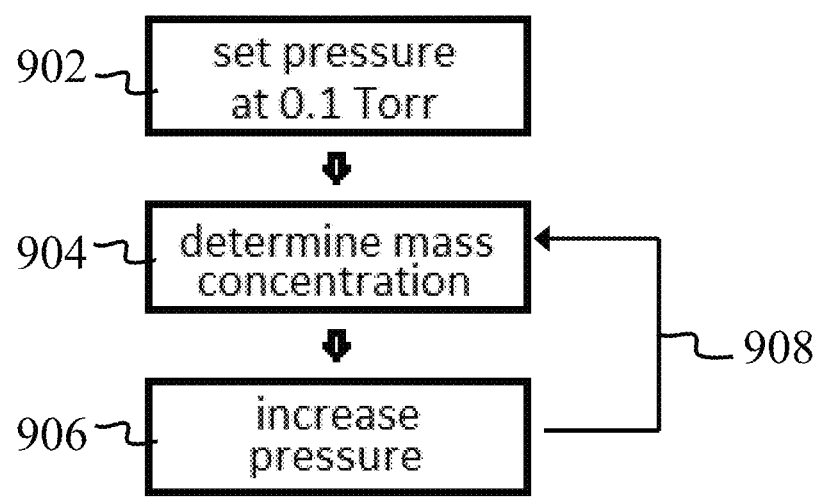
FIG. 9 is a flow diagram indicating a mode of measuring the mass of a sample component by adjusting operating pressure in accordance with embodiments of the present disclosure.

In one or more embodiments, wellbore measurements may be obtained by adjusting pressure within the mass analyzer of the MS depending on the concentration of molecules that is measured. With particular respect to FIG. 9, pressure may be iteratively modified in order to increase the analytical output from the sample. In one or more embodiments, pressure may be set to an initial value such as 0.1 Torr at 902. The sample may then be measured at 904 to determine mass concentration. Pressure may then be increased at 906 and then mass concentration may be determined at 904 through a number of iterations represented by 908.

The MS receives the separated components from the GC in a predictable order, often in which components become heavier and in lower concentration as a function of time. However, method in accordance with the present disclosure may account for anomalies from this pattern such as the presence of aromatic or branching components that may travel differently that the linear alkane counterparts, and the presence of various contaminants from mud filtrates and other wellbore fluid additives. In one or more embodiments, algorithms may be developed in which the RF frequency of the mass analyzer is adjusted following one or more mass spectrum measurements to increase sensitivity and resolution of individual components in mixtures eluted from the GC. For example ion trap and quadrupole mass analyzers are operated by applying a combination of RF and DC voltages to the electrodes of the respective mass analyzer to create a quadrupole electric field. This electric field traps ions in a potential energy well at the center of the analyzer. The mass spectrum is then acquired by scanning the RF and DC fields to destabilize low mass to charge ions. Destabilized ions are ejected through a hole in one endcap electrode and strike a detector, which allows a mass spectrum to be generated by scanning the fields so that ions of increasing m/z value are ejected from the cell and detected.

Figure 10:
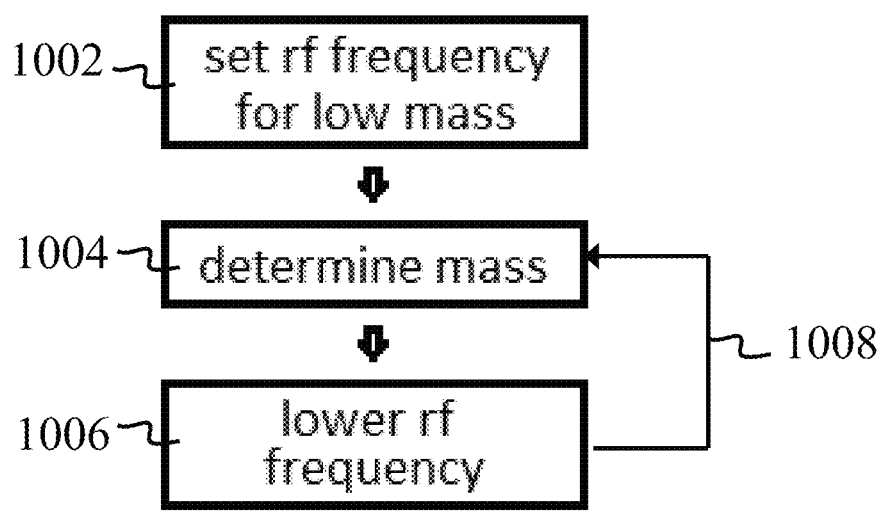
FIG. 10 is a flow diagram indicating a mode of measuring the mass of a sample component by adjusting radio frequency (RF) in accordance with embodiments of the present disclosure.

With particular respect to FIG. 10, a workflow for iteratively adjusting the RF of a mass analyzer in order to analyze heavier components is shown. However, at different RF frequencies the fragmentation pattern might be different too. In some embodiments, two or more RF may be used intermittently during operation in order to determine if altering the RF presents a differing fragmentation pattern that enables additional compounds to be resolved. For example, during measurement, the MS may be operated at a RF frequency suitable for detecting low mass components at 1002. Following the initial measurement, the mass of the sample components is determined at 1004, and the RF frequency is lowered at 1006, and mass is again determined at 1004. The RF modulation and mass determination may be performed iteratively according to 1008 until the operator is satisfied that all components of the sample have been identified and/or the error has been lowered to an acceptable lever. Furthermore, other variables like vacuum strength can be adjusted to optimize the outcome of each measurement. Furthermore, to expand the detection range the sample concentration can be reduced by dilution or other methods. All these automatic adaptations can be done automatically as a gradual or a stepwise change.

In the following section, the individual components of wellbore measurement tools will be discussed in greater detail in the following sections.

Gas Chromatograph

Gas chromatographs (GC) in accordance with the present disclosure may be installed within a wellbore tool as discussed above with respect to FIGS. 1 and 2. GC devices may contain a gas source that generates and maintains an inlet pressure for the gas chromatograph between 750 to 4500 Torr in some embodiments. Carrier gases include inert gases such as helium, hydrogen provided from a compressed gas cylinder or charged metal hydrides. Carrier gas sources may include a fraction of an ionizable gas such as nitrogen that is included at a concentration of 0.1% to 10% by volume of the total carrier gas in some embodiments, and from 1% to 3% in some embodiments.

Gas Chromatograph Detectors

GC in accordance with the present disclosure may include a thermal conductivity detector to analyze gaseous and fluid components. TCD detectors may be limited to certain carrier gases such as helium or hydrogen and may be unable to differentiate some components in a sample. TCDs may also have a lower detection limit of about 500 ppm.

In one or more embodiments, systems in accordance with the present disclosure may operate under work under reduced pressure and downhole temperatures. Systems may contain a gas chromatograph, a TCD, and a high pressure ($>10^{-3}$ bar) mass spectrometer. In some embodiments, systems may be designed to fit within a tool that may be emplaced within a wellbore, including as part of a tool string.

In one or more embodiments, the inlet of the TCD may be connected to the output of the GC column. In some embodiments, the inlet of the MS may be connected to the outlet of the TCD or directly from the GC. MS in accordance with the present disclosure may contain an ionizer, a mass analyzer, and an ion detector. The mass analyzer of the MS may be an ion trap analyzer in some embodiments, or a quadrupole mass analyzer in other embodiments. Connections between the individual components may be gas- or fluid-tight seals suitable for the application.

Mass Spectrometer

In one or more embodiments, devices in accordance with the present disclosure may include high pressure mass spectrometers such as quadrupole and ion trap mass spectrometers. MS in accordance with the present disclosure often contain several components, including an inlet, an ion source, a mass analyzer, and an ion detector. In some embodiment, MS may include a controller to activate the detector, one or more pumps, and a vacuum system to maintain pressure levels. Vacuum systems may include scroll pumps, a hydrogen generator such as metal hydride or a combination of both.

In one or more embodiments, the vacuum system may generate a pressure in an MS between the 0.001 Torr and 10 Torr and capable of handling an inlet pressure for the mass spec which is below 600 Torr. In some embodiments, a flow restrictor maybe placed between the outlet of the TCD and the mass spectrometer to maintain pressure at the TCD. MS in accordance with the present disclosure may include a second gas source with an ionizable gas such as nitrogen that is added just before the mass spectrometer. For example, after the TCD if the MS is connected to the outlet of TCD or after the column if the mass spectrometer is directly connected to the outlet of the column. MS in accordance with the present disclosure may operate at in a pressure regime that ranges from $10^{-3}$ to 10 Torr in some embodiments, and from $10^{-2}$ to 10 Torr in other embodiments.

Ion Sources

MS in accordance with the present disclosure may include an ionizer that ionizes the incoming analyte from the GC. Ionizers may include a soft ionizers that remove a single electron from molecules within the analyte and attempt to minimize molecule fragmentation, creating what is often referred to as a singly-charged molecular ion. For example, helium carrier gas from the GC may be used to induce chemical ionization of the analyte. In one or more embodiments, additional gas that can easily be ionized may be added to the analyte prior to passage to the ionizer to increase the degree of sample ionization. In some embodiments, nitrogen may be used to induce chemical ionization of the analyte.

Soft ionization techniques such as glow discharge ionization, electrospray ionization, photionization, electron ionization, and chemical ionization, may be used in devices in accordance with the present disclosure to produce ions from hydrocarbons and other analytes, and are discussed in further detail below.

A glow discharge ionization source includes a discharge chamber having an entrance orifice for receiving the analyte particle beam or analyte vapors, and a target electrode and discharge electrode therein. An electric field applied between the target electrode and discharge electrode generates an analyte ion stream from the analyte vapor, which is directed out of the discharge chamber through an exit orifice and into a mass analyzer.

In electro spray ionization, a sample solution enters an electrospray chamber through a hollow needle which is maintained at a few kilovolts relative to the walls of the electrospray chamber. The electrical field charges the surface of the liquid emerging from the needle, dispersing it by coulomb forces into a spray of fine, charged droplets. At this point the droplets become unstable and break into daughter droplets. This process is repeated as solvent continues to evaporate from each daughter droplet. Eventually, the droplets become small enough for the surface charge density to desorb ions from the droplets into the ambient gas. These ions, which include cations or anions attached to solvent or solute species which are not themselves ions, are suitable for analysis by a mass spectrometer.

Photon Ionization is another ionization technique in which analytes absorb light (typically a single photon in the vacuum ultraviolet range), and that photon energy is used to eject an electron. If the photon energy is just above the ionization potential, little energy will be leftover for fragmentation, providing soft ionization.

In electron ionization, an electron beam is directed at the analyte-containing sample. Some of the translational energy of the electrons is used to ionize the analytes. Typically 70 eV electrons are used, but that energy is much greater than typical ionization potentials (around 10 eV), and that excess energy typically leads to extensive fragmentation. Using low electron energy (around 15 eV) produces fewer fragments with less ionization efficiency.

In chemical ionization various gases are first ionized (typically using electron ionization), and those ionized gases are allowed to react with the analytes. Some of those reactions result in transferring an electrical charge to the analyte, resulting in ionized analytes. The efficiency of this process may vary greatly for different analytes (which could provide an important contrast mechanism), and often aggregates of the analyte and the ionization gas are formed (which can make analysis more complicated).

Mass Analyzers

Mass spectrometers in accordance with the present disclosure may include mass analyzers such as ion traps, linear and ion trap quadrupole, and Loeb-Eiber filters.

Quadrupole mass spectrometers (QMS) are designed from four cylindrical rods electrically connected to RF and DC voltage sources as discussed above with respect to FIGS. 6.1 and 6.2. The RF to DC ratio allows selective transmission of ions of a particular m/z value to travel in a stable trajectory along the z-axis. A mass spectrum is obtained by ramping the amplitude of the RF and DC voltages to sweeps ions of increasing m/z toward the detector.

A quadrupole ion trap (QIT) mass analyzer operates according to similar principles as a QMS, but may allow ions of multiple m/z values to be trapped simultaneously in a region of stability defined by solutions of the Mathieu equations described by, in some embodiments, the parameters $q_z=4\ zV/mr^2\omega^2$ and $a_z=-8\ zU/mr^2\omega^2$ where z is the electric charge, V the amplitude of the RF voltage, U is the amplited of the DC voltage, m is the mass of the ion, r is the radius of the ion trap, and $\omega$ is the angular frequency of the RF potential. QIT mass analyzers in accordance with the present disclosure may eject trapped ions oscillating at frequencies proportional to the fundamental frequency $\omega$ when operating in mass selective instability mode, in sequence from low to high m/z values along the $q_z$ axis, with the DC potential held at zero, by ramping the amplitude of the RF voltage as $q_z$ approaches 0.908 whereupon they are ejected, as discussed above with respect to FIG. 7.

Cylindrical ion trap (CIT) mass analyzers may be function similarly to the QIT, with the exception that hyperbolic electrodes of the QIT are replaced by a flat ring electrode. In some embodiments, miniaturized CIT mass analyzers may compensate for the loss of trapping capacity resulting from the smaller trap radius by including an array of traps with identical radii, as discussed above with respect to FIG. 8 and in the examples below.

Mass analyzers may also include Loeb-Eiber filter such as those described in U.S. Pat. No. 7,772,546. Loeb-Eiber filters may be suited for operation at relatively high pressures. In one or more embodiments, the collisional dampening of ions up to the mass filter thermalizes the kinetic energy of the ions which makes the filtering more effective. In some embodiments, Loeb-Eiber filters may be fabricated using traditional manufacturing techniques or MEMS technology.

Detectors

Mass spectrometers in accordance with the present disclosure may incorporate one or more detectors that measure ionized analyte components. Detectors may measure ions based upon their charge or momentum. In one or more embodiments, detectors may include a Faraday cup that measures ion current traveling through the mass analyzers of the mass spectrometer. Other detectors may include electron multipliers, channeltrons and multichannel plates.

EXAMPLES

In the following examples, an analyte is measured using a high-pressure gas chromatograph/mass spectrometer combination tool and MS is used to increase the accuracy of component identification and deconvolve multiple overlapping peaks in some instances.

A sample taken from the headspace of a dead oil sample containing hydrocarbon mixtures of components C1 to C8 and measured using a GC-MS in accordance with the present disclosure. The GC component of the device utilized an alumina BOND/$Na_2SO_4$ column and is using helium as a carrier gas. The MS component was equipped with a glow discharge ionizer and a miniature ion trap mass analyzer, and a faraday cup detector. During operation, the GC column was cycled at 60° C. for 2 minutes, then heated to 200° C. at 10° C./min for 10 minutes. The MS ion trap was operated at a starting RF of 6.97 MHz and an internal operating pressure of 3 Torr. The MS measurements were done with a frequency of 2 measurements per second with every measurement averaging 15 mass scans at each of the three RF frequencies.

Figure 11:
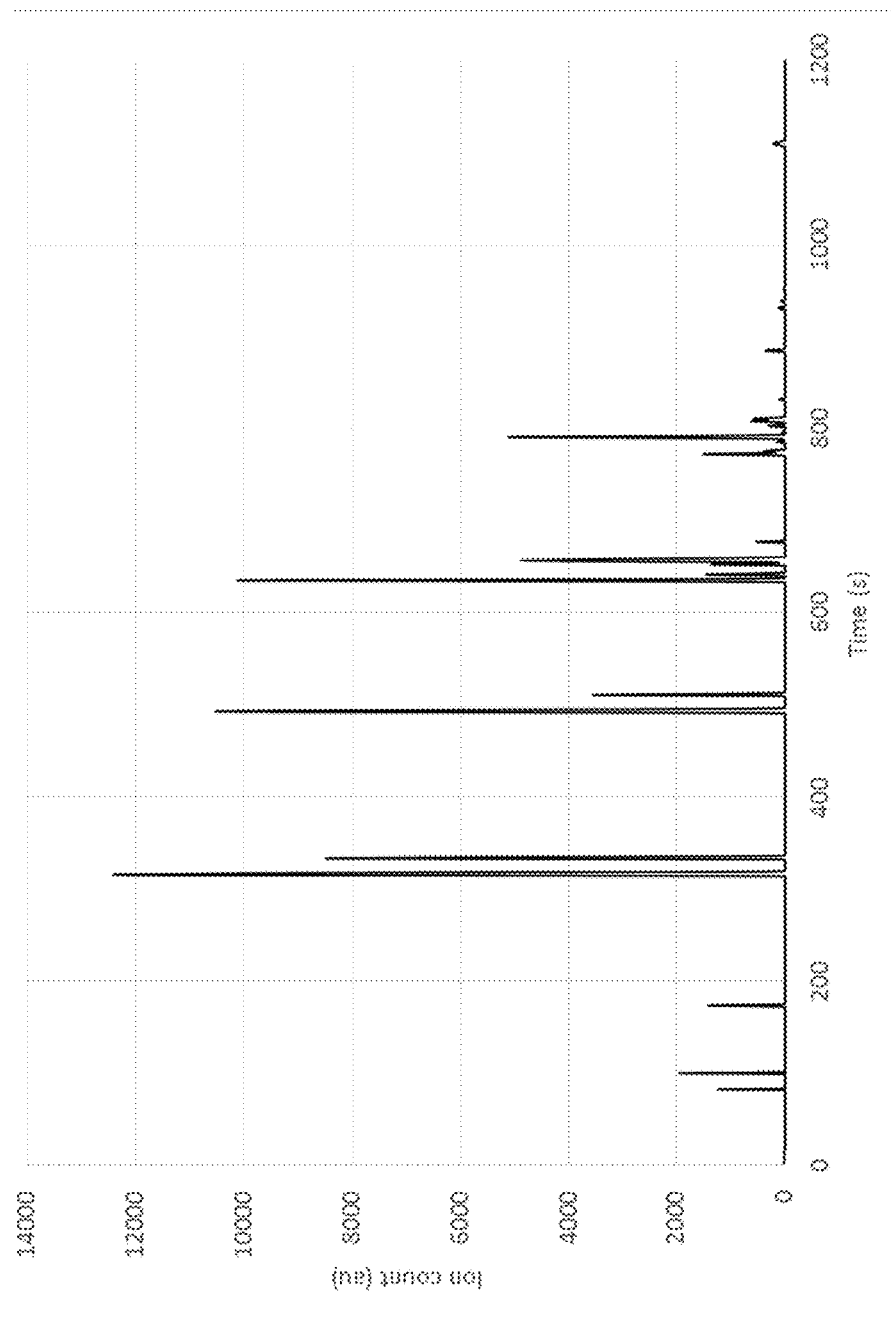
FIG. 11 is a graphical representation of the total ion count for a sample in accordance with embodiments of the present disclosure.
Figure 12:
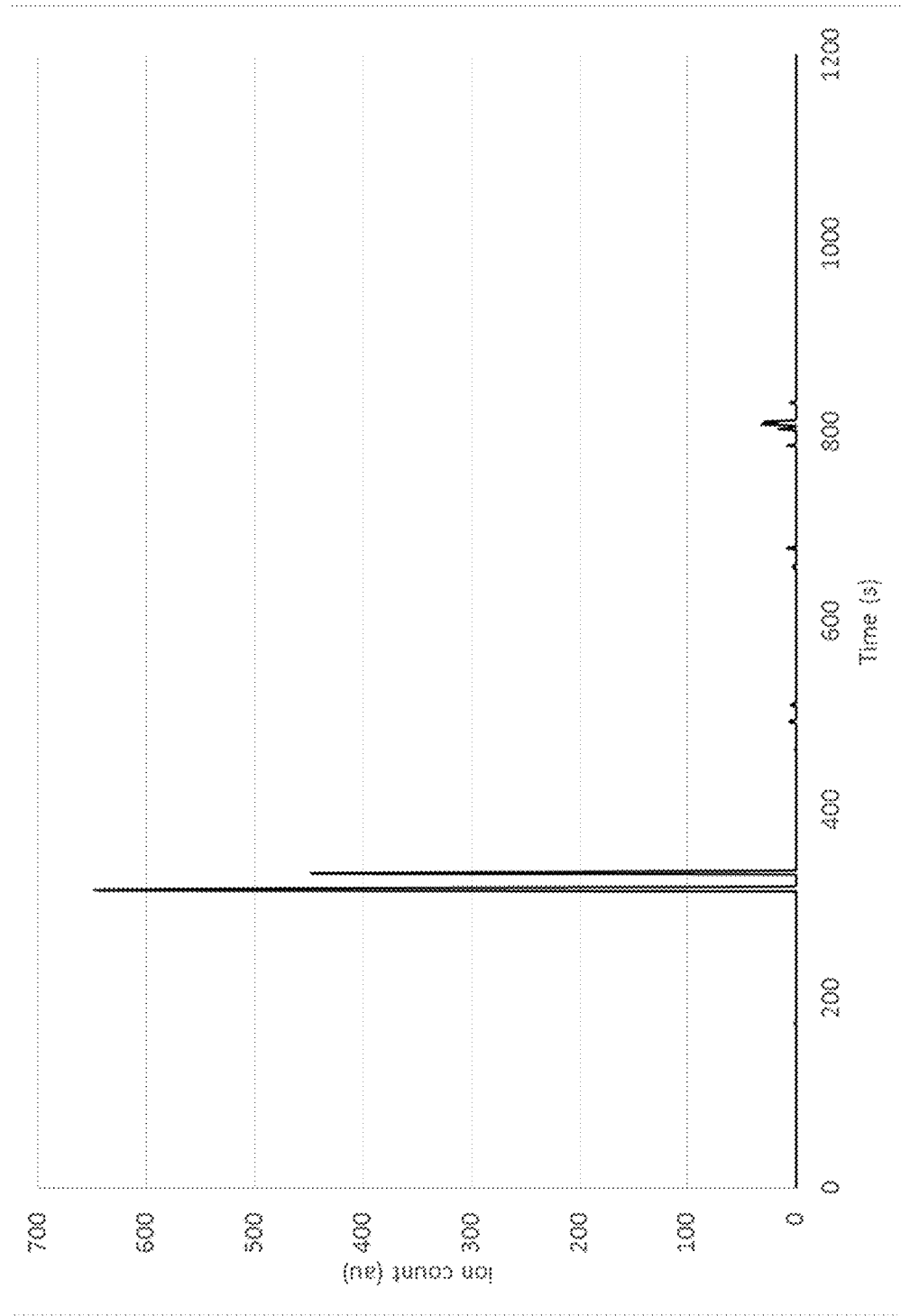
FIGS. 12-13 are graphical representations of the specific ion measurement at 58 m/z for a sample in accordance with embodiments of the present disclosure.
Figure 13:
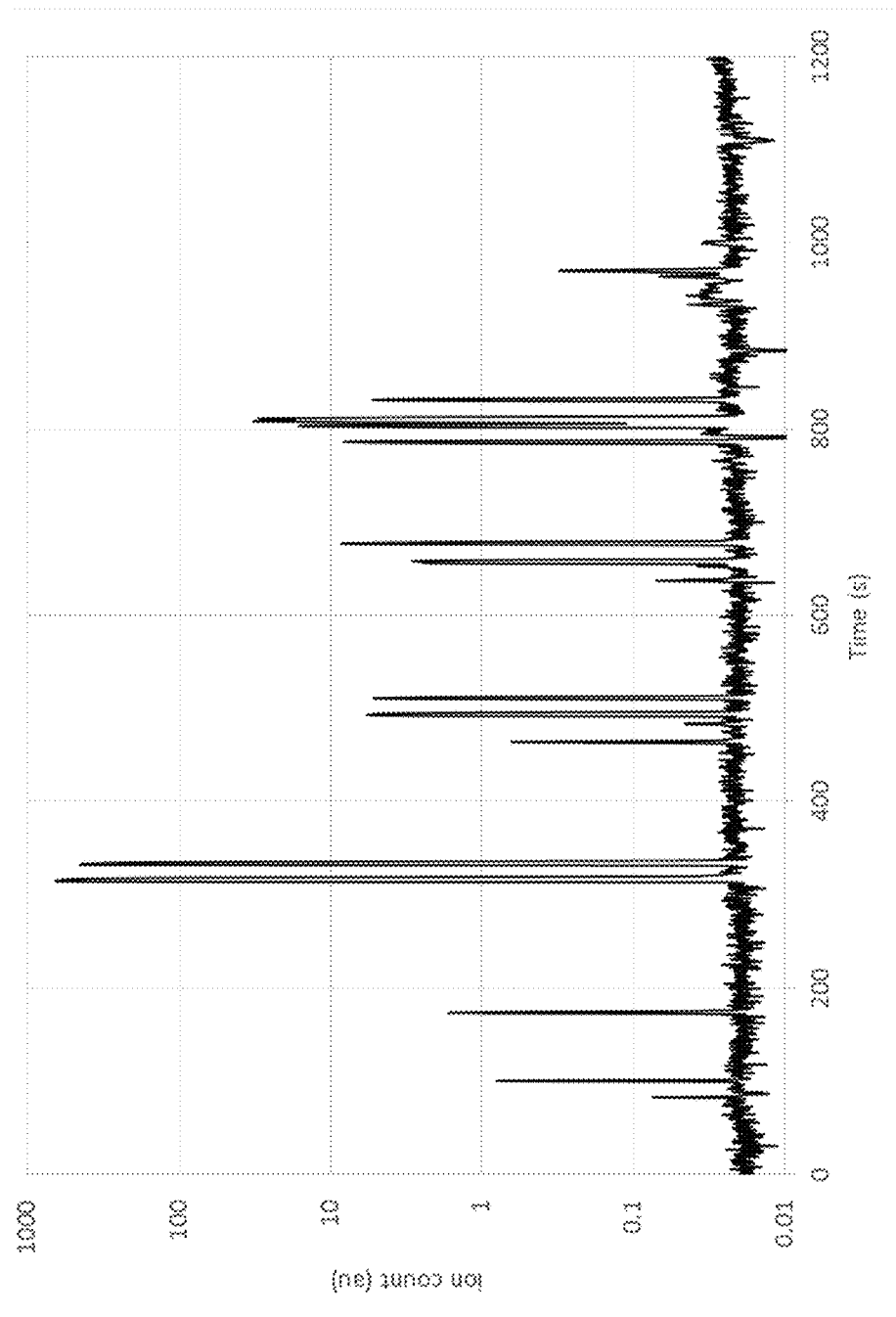
Figure 14:
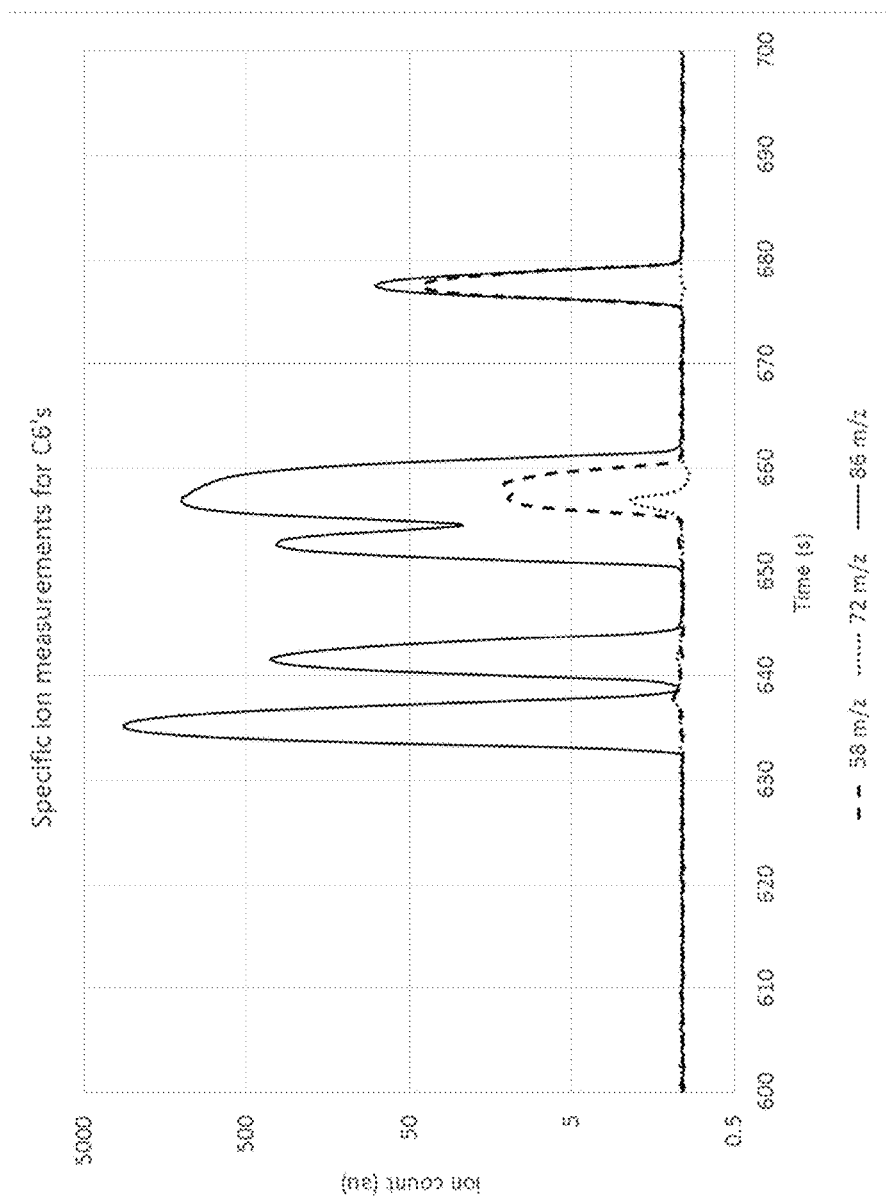
FIG. 14 is a graphical representation of specific ion measurement at 58 m/z, 72 m/z, and 86 m/z for a sample in accordance with embodiments of the present disclosure.

With particular respect to FIG. 11, a diagram for the total ion count (TIC) for the sample is shown at a frequency of 6.97 MHz. With particular respect to FIG. 12, the specific ion measurement at 58 m/z is shown for the same sample. FIG. 13 also shows the sample measured in FIG. 12 with the total ion count according to a logarithmic scale. With particular respect to FIG. 14, the GC fraction at 665-660 seconds, which correlates to C6 hydrocarbons, is analyzed with MS at 58 m/z, 70 m/z, and 86 m/z. The results demonstrate that it is possible to deconvolve the co-eluting fractions between 650 and 660 seconds from the GC. Furthermore, the spectrum demonstrates that it is possible to distinguish n-C6 at 680 seconds from the other C6 isomers by observing the particular fragmentation pattern.

Figure 15:
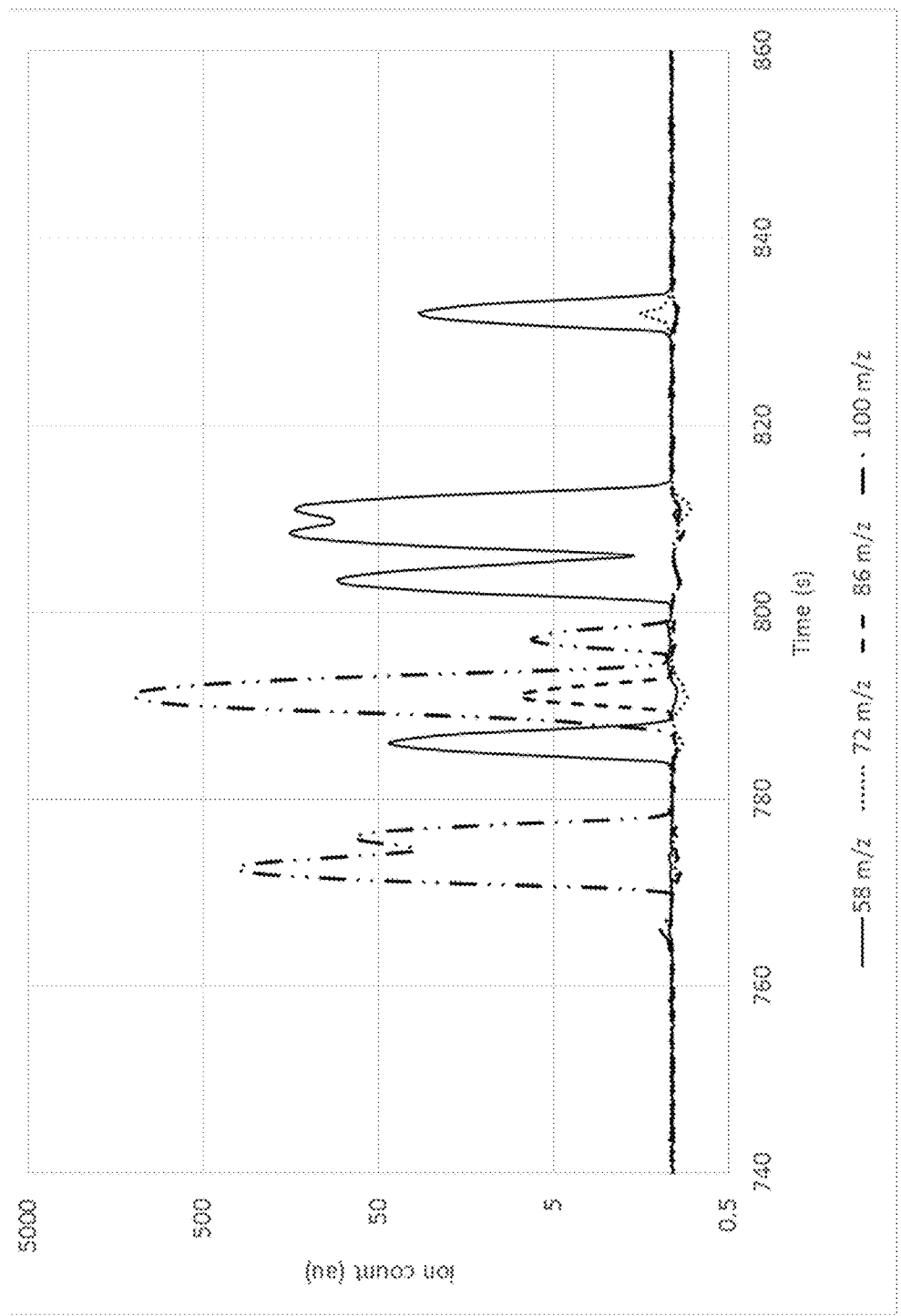
FIG. 15 is a graphical representation of specific ion measurement at 58 m/z, 72 m/z, 86 m/z, and 100 m/z for a sample in accordance with embodiments of the present disclosure.
Figure 16:
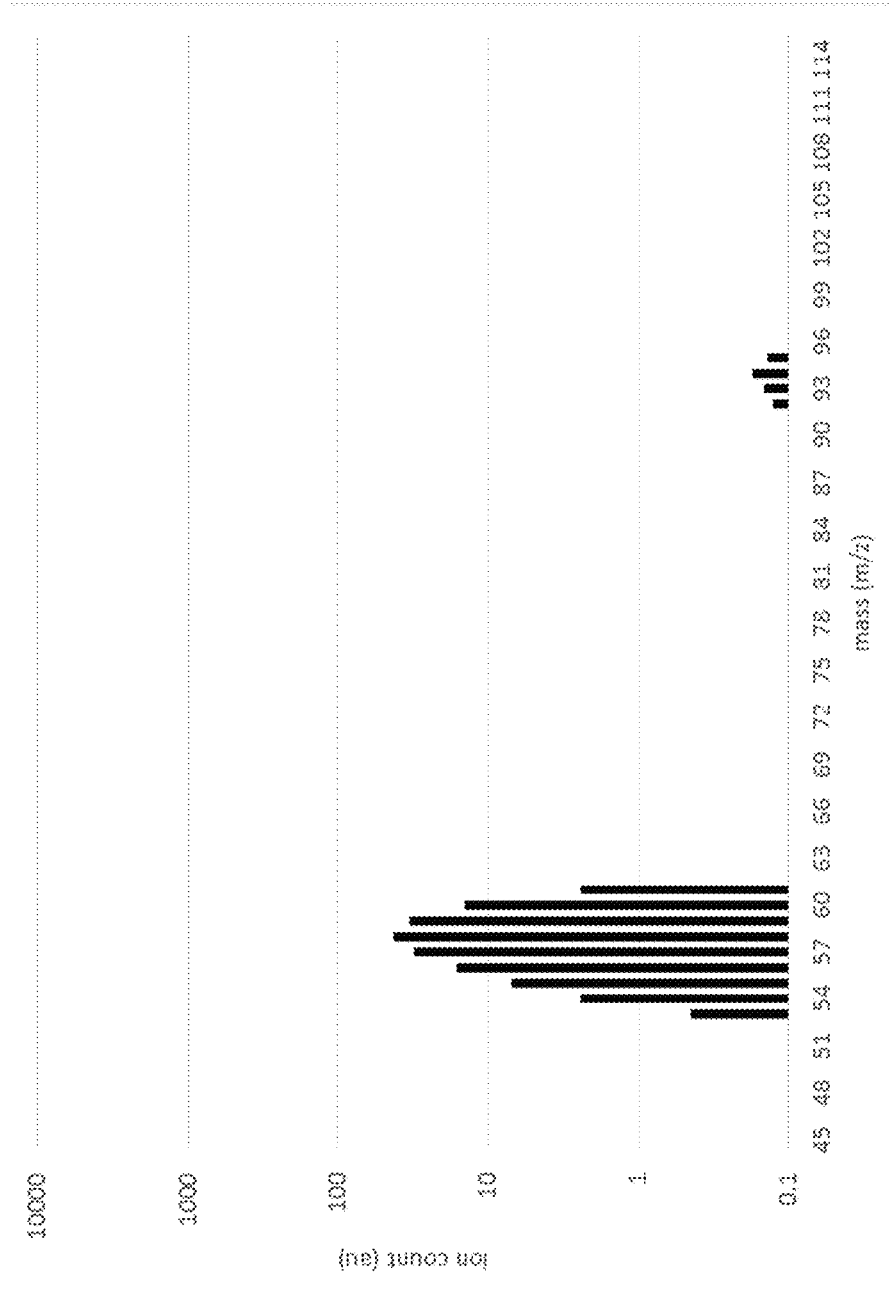
FIGS. 16-18 are mass spectra of three C7 components eluting at 786, 792, and 797 RF, respectively, for a sample in accordance with embodiments of the present disclosure.
Figure 17:
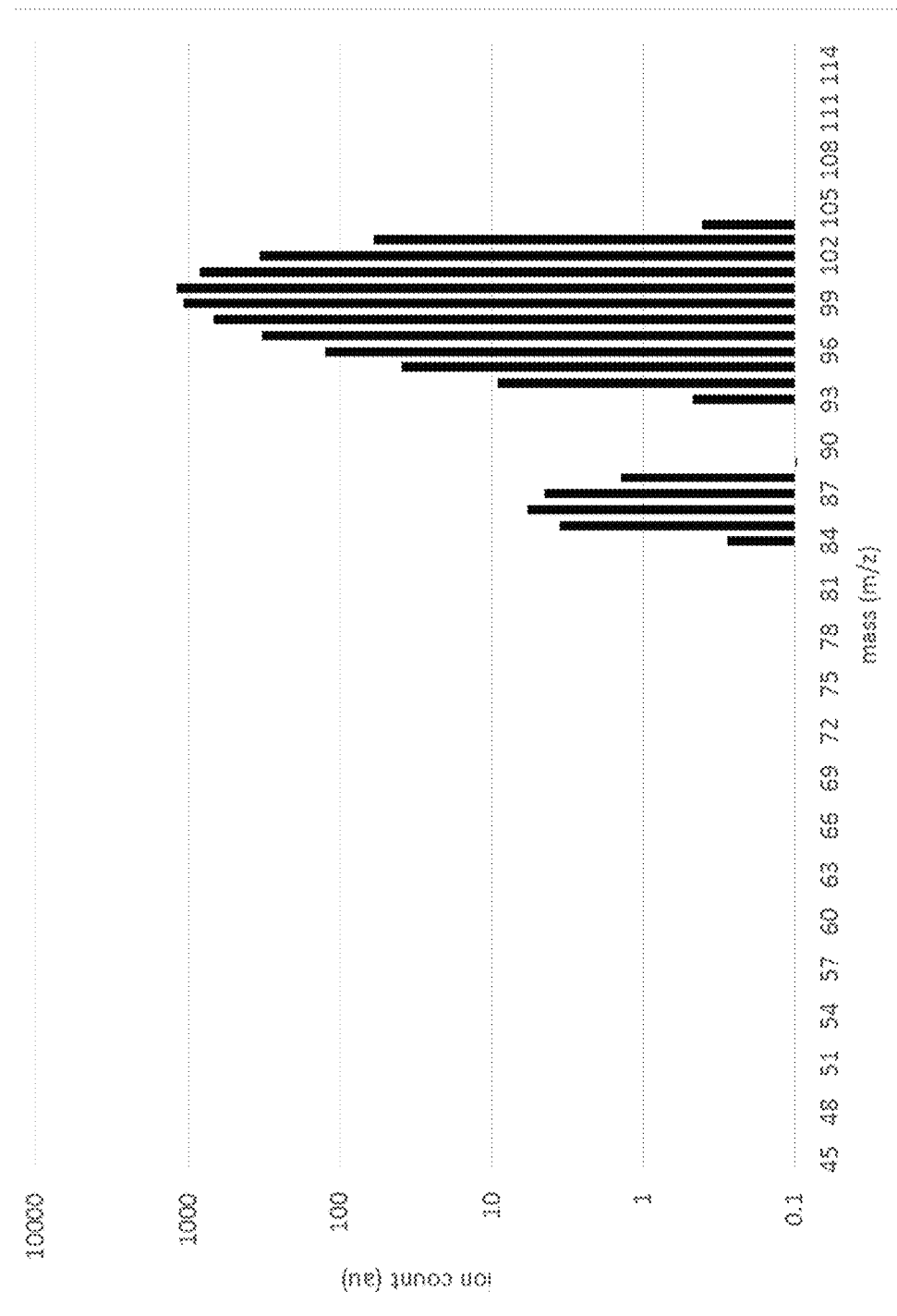
Figure 18:
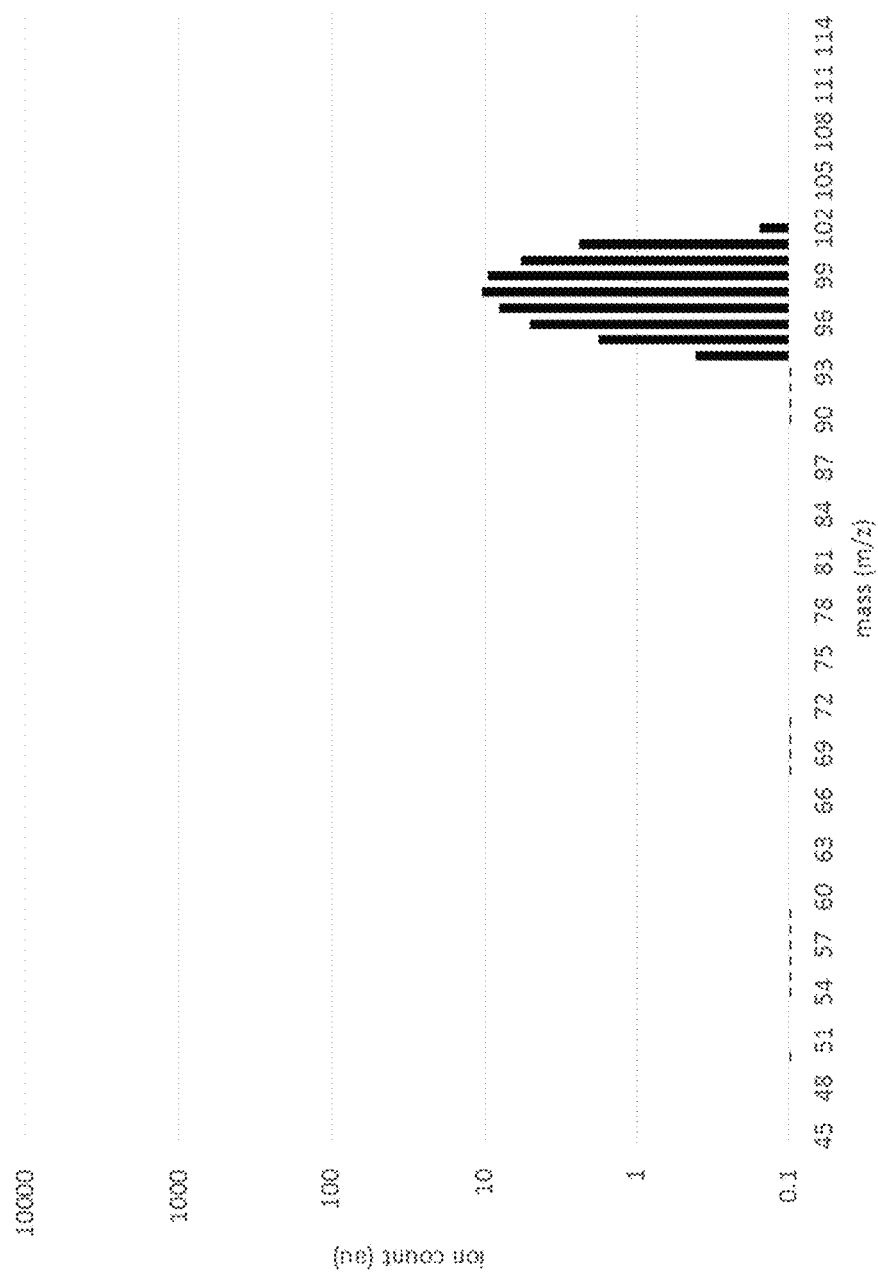

In the next example, combined GC-MS is used to resolve the peaks for the same sample. The specific ion measurement is shown for the C7 fraction from the GC at 58 m/z, 72 m/z, 86 m/z, and 100 m/z are shown in FIG. 15. With particular respect to FIGS. 16-18, the mass spectrum of three C7 components eluting at 786, 792, and 797 seconds, respectively, are shown to demonstrate the ability of a GC-MS to resolve species that would overlap if a column or temperature regime is used with less resolving power than the current measurement. For example, overlap in spectra may be expected in cases in which downhole conditions involve high ambient temperatures and cooling is more difficult.

In accordance with some examples, applicant has discovered that by providing and combining certain features, including a rotary valve and an ion trap or quadrupole mass analyzer, it is possible to operate a mass spectrometer at high pressures (greater than $10^{-2}$ Torr). This in turn allows for more robust pumps (e.g., scroll pumps, screw pumps, piston pumps) which are—in contrast to typical mass spectrometry pumps—suitable for use in downhole conditions in a wellbore. It is further noted in this regard that the ion trap and quadrupole mass analyzers are scalable to small sizes that reduce the increased molecular collisions that occur due to higher pressures.

Although the preceding description has been described herein with reference to particular means, materials and embodiments, it is not intended to be limited to the particulars disclosed herein; rather, it extends to all functionally equivalent structures, methods and uses, such as are within the scope of the appended claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C.

§112(f) for any limitations of any of the claims herein, except for those in which the claim expressly uses the words 'means for' together with an associated function.

To the extent used in this description and in the claims, a recitation in the general form of "at least one of [a] and [b]" should be construed as disjunctive. For example, a recitation of "at least one of [a], [b], and [c]" would include [a] alone, [b] alone, [c] alone, or any combination of [a], [b], and [c].

The invention claimed is:

1. A wellbore tool comprising:
a gas chromatograph having a column configured to separate a fluid sample into at least partially separated components;
a rotary valve configured to inject the fluid sample into the gas chromatograph; and
a mass spectrometer configured to receive the at least partially separated components from the gas chromatograph, wherein the mass spectrometer is configured to operate downhole at a pressure greater than $10^{-2}$ Torr and wherein the mass spectrometer comprises at least one of (a) an ion trap analyzer and (b) a quadrupole mass analyzer.

2. The wellbore tool of claim 1, wherein the tool is present on a drill string.

3. The wellbore tool of claim 1, wherein the tool is a wireline tool.

4. The wellbore tool of claim 1, wherein the wellbore tool further comprises a vacuum source selected from a group consisting of scroll pumps, dry screw pumps, and piston pumps.

5. The wellbore tool of claim 1, further comprising a thermal conductivity detector.

6. The wellbore tool of claim 5, wherein an outlet of the gas chromatograph is configured to deliver an analyte into an inlet of the thermal conductivity detector and wherein an outlet of the thermal conductivity detector is configured to deliver the analyte into an inlet of the mass spectrometer.

7. The wellbore tool of claim 5, wherein an outlet of the gas chromatograph is bifurcated into a first stream and a second stream, and wherein the first stream is sent to an inlet of the thermal conductivity detector and wherein the second stream is sent to an inlet of the ion trap mass spectrometer.

8. The wellbore tool of claim 1, wherein an outlet of the gas chromatograph is configured to deliver an analyte into an inlet of the mass spectrometer.

9. The wellbore tools of claim 1, wherein the mass spectrometer comprises an ion trap mass analyzer.

10. The wellbore tool of claim 1, wherein the mass spectrometer comprises a quadrupole mass analyzer.

11. The wellbore tool of claim 1, wherein the mass spectrometer comprises a faraday cup detector.

12. The wellbore tool of claim 1, wherein a connection between the gas chromatograph and the mass spectrometer comprises an inlet for an ionizable gas from a gas source.

13. The wellbore tool of claim 1, wherein the mass spectrometer operates at a pressure within the range of $10^{-2}$ to 10 Torr.

14. A system comprising:
a gas chromatograph having a column configured to separate a fluid sample into at least partially separated components;
a rotary valve configured to inject the fluid sample into the gas chromatograph; and
a mass spectrometer configured to receive the at least partially separated components from the gas chromatograph, wherein the mass spectrometer is configured to operate at a pressure greater than $10^{-2}$ Torr and wherein the mass spectrometer comprises at least one of (a) an ion trap analyzer and (b) a quadrupole mass analyzer and wherein the mass spectrometer is controlled by a control module configured to adjust one or more of the pressure within the mass spectrometer and the operating radio frequency of a mass analyzer within the mass spectrometer.

15. The system of claim 14, further comprising a thermal conductivity detector.

16. The system of claim 15, wherein the outlet of the gas chromatograph is bifurcated into a first stream and a second stream, and wherein the first stream is sent to the inlet of the thermal conductivity detector and wherein the second stream is sent to the inlet of the ion trap mass spectrometer.

17. A method comprising:
emplacing a wellbore tool in a wellbore, the wellbore tool comprising a gas chromatograph having a column configured to separate a fluid sample into at least partially separated components, a rotary valve configured to inject the fluid sample into the gas chromatograph, and a mass spectrometer configured to receive the at least partially separated components from the gas chromatograph, wherein the mass spectrometer is configured to operate downhole at a pressure greater than $10^{-2}$ Torr and wherein the mass spectrometer comprises at least one of (a) an ion trap analyzer and (b) a quadrupole mass analyzer;
drawing the fluid sample from the wellbore into the wellbore tool; and
operating the gas chromatograph and the mass spectrometer to determine a molecular weight of one or more of the at least partially separated components of the fluid sample.

18. The method of claim 17, wherein the mass spectrometer comprises an ion trap mass analyzer.

19. The method of claim 17, wherein the mass spectrometer comprises a quadrupole mass analyzer.

* * * * *